United States Patent [19]

Takemoto et al.

[11] Patent Number: 4,684,745

[45] Date of Patent: Aug. 4, 1987

[54] PROCESS FOR PRODUCING α-L-ASPARTYL-L-PHENYLALANINE METHYL ESTER FOR ITS HYDROCHLORIDE

[75] Inventors: Tadashi Takemoto, Kawasaki; Yasuo Ariyoshi, Yokohama, both of Japan

[73] Assignee: Ajinomoto Company Incorporated, Tokyo, Japan

[21] Appl. No.: 484,506

[22] Filed: Apr. 13, 1983

[30] Foreign Application Priority Data

Apr. 22, 1982 [JP] Japan ................................. 57-67687

[51] Int. Cl.$^4$ ............................................ C07C 101/32
[52] U.S. Cl. ........................................ 560/41; 560/40
[58] Field of Search ................. 260/112.5 R; 424/177; 514/19; 560/40, 41

[56] References Cited

U.S. PATENT DOCUMENTS

| | | | |
|---|---|---|---|
| 3,786,039 | 1/1974 | Ariyoshi et al. | 560/41 |
| 3,798,207 | 3/1974 | Ariyoshi et al. | 560/41 |
| 3,879,372 | 4/1975 | Boesten | 560/39 |
| 3,933,781 | 1/1976 | Bachman et al. | 560/41 |
| 4,071,511 | 1/1978 | Takemoto et al. | 560/335 |
| 4,111,925 | 9/1978 | Bachman | 562/450 |
| 4,173,562 | 11/1979 | Bachman et al. | 560/41 |
| 4,348,317 | 9/1982 | Bachman | 560/41 |

FOREIGN PATENT DOCUMENTS 0058063 8/1982 European Pat. Off. .

OTHER PUBLICATIONS

Sheehan et al., *J. Am. Chem. Soc.*, 80, 1158 (1958).
Vigneaud et al., *J. Biol. Chem.*, 98, 577 (1932).

*Primary Examiner*—Johnnie R. Brown
*Assistant Examiner*—F. T. Moezie
*Attorney, Agent, or Firm*—Oblon, Fisher, Spivak, McClelland & Maier

[57] ABSTRACT

A process for producing α-L-aspartyl-L-phenylalanine methyl ester or its hydrochloride which comprises contacting N-formyl-α-L-aspartyl-L-phenylalanine methyl ester with a mixture of methanol and a highly concentrated hydrochloric acid at a temperature of between 0° and 40° C., whereby the amino-protecting formyl group is removed and α-L-aspartyl-L-phenylalanine methyl ester crystalizes, and isolating the hydrochloride crystals, and, if desired, converting the hydrochloride to free α-L-aspartyl-L-phenylalanine methyl ester, is disclosed along with variations thereof. The process is commerically advantageous in that it utilizes inexpensive materials while minimizing hydrolysis of the peptide bond.

6 Claims, No Drawings

PROCESS FOR PRODUCING α-L-ASPARTYL-L-PHENYLALANINE METHYL ESTER FOR ITS HYDROCHLORIDE

DETAILED EXPLANATION OF THE INVENTION

This invention relates to a process for producing α-L-aspartyl-L-phenylalanine methyl ester, which may be referred to as 'α-APM' hereinafter, or its hydrochloride. In particular, it relates to a process for producing α-APM or its hydrochloride which comprises (a) removing the formyl group, which may be referred to as 'For' hereinafter, efficiently and selectively from and α-APM of which the amino group is protected with a formyl group, i.e., N-formyl-α-L-aspartyl-L-phenylalanine methyl ester, which may be referred to as 'For-α-APM' hereinafter, in a methanol-hydrochloric acid mixture, i.e., in a methanolic hydrochloric acid, and (b) separating the thus-formed α-APM as its hydrochloride, i.e., α-L-aspartyl-L-phenylalanine methyl ester hydrochloride, which may be referred to as 'α-APM.HCl' hereinafter, and (c) changing the separated α-APM.HCl, if desired, to free α-APM. In this connection, change of α-APM.HCl to α-APM may be carried out by a conventional method.

This invention provides a useful means of synthesizing a dipeptide sweetener and more specifically an efficient method of removing the For from formyl group-α-APM.

Incidentally, For-α-APM may be easily produced from condensation between N-formyl-L-aspartic acid anhydride and L-phenylalanine methyl ester, as an intermediate for synthesis of α-APM. See Japanese Pat. Appl. Kokai No. 23,001/1977, corresponding to U.S. Pat. No. 4,071,511, etc.

An N-formyl group, i.e., a formyl group protecting an amino group, has heretofore been removed with the use of dilute hydrochloric acid, hydrogen peroxide (G. Losse et al., Ann. Chem., 636, 140 (1960)), hydrazine (P. Lefrancier et al., Bull. Soc. Chim. France, 1965, 3668), aniline (R. Geiger et al., Chem. Ber., 102, 2487 (1969)) or hydroxylamine (R. Geiger; Chem. Ber., 101, 3386 (1968)), or by catalytic reduction (G. Losse et al., J. Prakt. Chem., 24, 118 (1964), for example.

Among these methods of deformylation, the one where dilute hydrochloric acid is used is easy to operate as well as inexpensive and, accordingly, is a commercially excellent method. The dilute hydrochloric acid deformylation process is usually carried out, as follows. In connection with simple compounds such as N-formyl amino acids, acidic hydrolysis is employed where a compound to be deformylated is heated with dilute hydrochloric acid (V. du Vigneaud et al.; J. Biol. Chem., 98, 577 (1932)), while, in connection with N-formyl peptides, acidic-alcoholic hydrolysis is employed where, e.g., a compound to be deformylated is allowed to stand in a methanolic hydrochloric acid having a normality of not more than 0.5 at room temperature for 48 hours, whereby the peptide bond is prevented from splitting (J. C. Sheehan et al.; J. Am. Chem. Soc., 80, 1158 (1958)).

However, in connection with N-formyl peptides, like For-α-APM, which have both an ester group and a free carboxyl group as well as an amino group protected with a formyl group, the ester and peptide bonds are also hydrolyzed if deformylation is carried out by acidic hydrolysis, while the free carboxyl group is esterified if deformylation is carried out by acidic-alcoholic hydrolysis. The latter hydrolysis is also commercially disadvantageous because a long period of time is required for the deformylating hydrolysis, e.g., as long as 48 hours. See Japanese Pat. Appln. Kokoku No. 17,727/1979, corresponding to U.S. Pat. No. 3,879,372.

The inventors already proposed some improvements in the deformylation whereby such difficulties are overcome to some extent, e.g., the hydxoxylamine-strong acid addition salt method (Jap. Pat. Appln. Kokai No. 68,520/1976, corr. to U.S. Pat. No. 4,024,418) and the aqueous organic solvent-strong acid mixture method (Jap. Pat. Appln. Kokai No. 23,001/1977, referred to hereinabove). These methods are, however, still commercially disadvantageous in that hydroxylamine is required for the former and an organic solvent for the latter. The inventors further investigated to propose a commercially advantageous deformylation reaction devoid of the abovementioned difficulties and found that, if For-α-APM is heated in a 0.5~3N strong acid at 70°~150° C., deformylation takes place selectively and is completed in a short period of time such as 15 seconds~60 minutes, while side-reactions such as hydrolysis of the ester or peptide bond suppressed. See Japanese Pat. Appln. Kokai No. 131,746/1982. The last-mentioned deformylation is still not satisfactory enough, because the ester bond is still hydrolized to some degree.

The inventors further investigated to propose another commercially advantageous method of removing the N-formyl group devoid of all the above-mentioned difficulties and found that, if deformylation reaction is carried on by bringing For-α-APM into contact with a mixture of methanol and a highly concentrated hydrochloric acid at a temperature of between 0° and 40° C., while the α-APM formed is being successively crystallized and eliminated from the reaction system as its sparingly soluble hydrochloride, side-reactions such as hydrolysis of the ester or peptide bond or esterification of the free carboxyl group are suppressed and high overall yields are attained for α-APM accordingly. A first embodiment of this invention has been made on the basis of these findings.

The process of this invention may be applied advantageously, when α-APM is commercially produced from a precursor compound having a formyl group as the amino-protecting group. According to processes for producing α-APM with the use of formyl group as the amino-protecting group, there is usually involved condensation between N-formyl-L-aspartic acid anhydride and L-phenylalanine methyl ester. This reaction gives, however, not only For-α-APM, a precursor of the desired α-APM, but also N-formyl-β-L-aspartyl-L-phenylalanine methyl ester, which is isomeric with For-α-APM and may be referred to as 'For-β-APM' hereinafter.

An example of conventional methods of isolating the desired α-APM comprises treating a mixture of For-α-APM and For-β-APM with a methanol and dilute hydrochloric acid mixture, neutralizing the resulting solution to precipitate the α-APM and isolating the α-APM from the remainder. According to this method, however, the above-mentioned side-reactions will take place because α-APM.HCl is not precipitated during the treatment, and, when the α-APM is isolated after neutralization, part of it remains in the mother liquor in almost the same amount as the β-APM because α-APM and β-APM (i.e., β-L-aspartyl-L-phenylalanine methyl ester) are almost the same in solubility.

In that case, however, if a process of this invention is employed, α-APM.HCl and, accordingly, also α-APM may be efficiently obtained with purification, because, if a mixture of For-α-APM and For-β-APM is brought into contact with a mixture of methanol and a highly concentrated hydrochloric acid, the formyl groups are split to give α-APM and β-APM as time passes, while the α-APM formed is being successively crystallized and eliminated from the reaction system as its sparingly soluble hydrochloride, and, accordingly, the α-APM undergoes almost no side-reactions, while the β-APM is retained in the mother liquor. Incidentally, in connection with the fact that α-APM.HCl is very difficult to dissolve in hydrochloric acid, see U.S. Pat. No. 3,798,207 corresponding to Japanese Pat. Applin. Kokoku No. 41, 525/1974.

In connection with the deformylation conditions according to this invention, it has been found that, as the results of the inventors' study of the deformylation being carried out under various reaction conditions, the deformylation is remarkably affected by concentrations of hydrochloric acid and methanol and reaction temperature.

According to the inventors' findings, if the hydrochloric acid concentration is too low, α-APM-HCl is precipitated only in small amounts while side-reactions such as hydrolysis of the ester bond occur. On the other hand, if the hydrochloric acid concentration is too high, the peptide bond and the ester group are hydrolyzed as rapidly as the formyl group is removed.

In connection with the reaction temperature, if it is too high, the peptide bond and the ester group are hydrolyzed as rapidly as the formyl group is removed and α-APM.HCl is also precipitated in small amounts.

In connection with the methanol concentration, if it is too low, the ester group undergoes hydrolysis, and, on the other hand, if it is too high, the free carboxyl group undergoes methyl-esterification and α-APM.HCl is also precipitated in small amounts.

In connection with the reaction time, too short a reaction time results in insufficient deformylation, and, on the other hand, too long a reaction time is disadvantageous from the commercial view point.

In consideration of these facts, a hydrochloric acid concentration range of 2 to 12 normal(N), preferably 5 to 8 normal(N), a methanol concentration range of 5 to 60% by volume, preferably 10 to 30% by volume, on the basis of the volume of the hydrochloric acid used, and a reaction temperature range of 0° to 40° C. have been chosen as preferred deformylation reaction conditions. Under these conditions, the deformylation will be completed in a reaction time range of 1 to 5 days.

The Examples 5, 6 and 11 to 17 are examples of the first embodiment of this invention.

The inventors have found, as the result of their further investigation, that the above-described first embodiment of this invention, when modified in some respects, gives better effects, and have completed on these findings second and third embodiments of this invention.

According to this invention, the said second embodiment comprises a heating pretreatment where a mixture of For-α-APM, methanol and a highly concentrated hydrochloric acid is once heated to, and kept at, elevated temperatures for a short time prior to the deformylation of the For-α-APM at a temperature of between 0° and 40° C. From the practical point of view, the elevated temperature is between 50° and 100° C. and the short time is a period of time not longer than 30 minutes.

By the heating treatment, precipitation of α-APM.HCl may further be facilitated, and the time required for deformylation may be shortened from the above-mentioned period of 1 to 5 days to a period of 1 to 3 days.

Example 3 is an example of the second embodiment of this invention.

The said third embodiment of this invention is a modification of the second embodiment, where the same heating treatment is carried out with the same temperature and time but with a highly concentrated hydrochloric acid having a little lower concentration and a highly concentrated hydrochloric acid is further added sometime after the heating treatment. In this modification, the said 'a little lower concentration' means a concentration of about 2 to 6 normal(N), and, accordingly, methanol is used in slightly increased amounts, i.e., in a concentration range of 10 to 70% by volume, preferably 30 to 55% by volume, on the basis of the volume of the hydrochloric acid used. Hydrochloric acid is desirably used in an amount of 0.5 to 3 moles, preferably about 1 to 1.3 moles, per mole of For-α-APM. A highly concentrated hydrochloric acid is further added in such amounts as adjust the hydrochloric acid concentration in the reaction mixture to 2 to 12 normal(N), preferably 5 to 8 normal(N). Such further addition is, as has been mentioned, carried out sometime after the heating treatment. In greater detail, it is usually added after the heated reaction mixture has been cooled, though it may be added prior to, or during, the cooling.

The modification brigs about further suppression of side-reactions, in addition to the above-mentioned facilitated precipitation of α-APM.HCl and shortened time required for deformylation, and, accordingly, higher yields of α-APM.HCl and also free α-APM.

α-APM hydrochloride thus obtained may be used as such as a sweetener (Japanese Pat. Appln. Kokai No. 13, 371/1974). It is, however, usually converted to free α-APM by neutralizing with the use of an alkali such as sodium carbonate in an aqueous solvent which is collected as free α-APM crystals.

As is evident from the foregoing, this invention provides a commercially very useful process for producing α-APM.HCl or α-APM, because, in accordance with this invention, the desired deformylated peptide may be produced, in the same or more isolation yields than those achieved in accordance with the conventional prior arts processes, by removing the formyl group from For-α-APM, the formed α-APM being crystallized as its sparingly soluble hydrochloride, with the use of only inexpensive reagents such as hydrochloric acid and methanol, and finally isolating the hydrochloride.

This invention will be further explained by the following examples.

EXAMPLE 1

A mixture of 15 ml methanol and 40 ml 4N hydrochloric acid was heated to 60° C. 48.3 g For-α-APM was added to the heated mixture. The resulting mixture was kept at this temperature for 15 minutes, cooled rapidly to 25° C., mixed with 28 ml concentrated hydrochloric acid, and stirred at 25° C. for 2 days. The mixture was further stirred at 5° C. for 3 hours.

The precipitated α-APM.HCl dihydrate crystals were isolated from the remainder by filtering.

The α-APM content in the crystals was 36.1 g when measured with an amino acid analyser (Type 835, Hitachi, Ltd.), which weight in turn corresponds to a 81.8% yield on the basis of the For-α-APM.

Incidentally, it is to be added that α-L-aspartyl-L-phenylalanine methyl ester hydrochloride (α-APM.HCl) is usually crystallized from an aqueous solution in the dihydrate form (α-APM.HCl.2H$_2$O).

EXAMPLE 2

To a mixed solvent of 10 ml methanol and 17 ml water was added a mixture of 32.2 g For-α-APM and 8.1 g For-β-APM. The resulting mixture was heated to 85° C., mixed with 10 ml concentrated hydrochloric acid, kept at the temperature for 5 minutes, and cooled rapidly to 20° C. The cooled mixture was, after being mixed with 20 ml concentrated hydrochloric acid, stirred at 20° C. for 2 days and then further stirred at 5° C. for 3 hours.

The formed α-APM.HCl dihydrate crystals were isolated by filtering.

The α-APM moiety in the crystals was 23.4 g, which weight in turn corresponds to a 79.5% yield on the basis of the For-α-APM. No β-APM was detected.

EXAMPLE 3

A mixed solvent of 15 ml methanol and 65 ml 7N hydrochloric acid was heated to 65° C., mixed with 48.3 g For-α-APM and kept at this temperature for 10 minutes. The resulting mixture was cooled rapidly to 20° C., and stirred at the temperature for 1 day and then at 5° C. for 3 hours.

The precipitated crystals were collected by filtering.

The α-APM moiety in the crystals was 34.0 g, which weight in turn corresponds to a 77.0% yield on the basis of the For-α-APM.

EXAMPLE 4

A mixed solvent of 15 ml methanol, 25 ml water and 14 ml concentrated hydrochloric acid was heated to 60° C., added with 48.3 g For-α-APM and kept at this temperature for 15 minutes.

The resulting mixture thus treated was rapidly cooled to 20° C., added with 28 ml concentrated hydrochloric acid and stirred at this temperature for 2 days and then at 5° C. for 3 hours.

The formed crystals were collected by filtering.

The α-APM content in the crystals was 35.0 g. This weight corresponds to a 79.3% yield on the basis of the For-α-APM.

EXAMPLE 5

To a mixed solvent of 15 ml methanol, 25 ml water and 42 ml concentrated hydrochloric acid was added 48.3 g For-α-APM. The mixture was stirred at 25° C. for 4 days and further at 5° C. for 3 hours.

The crystallized α-APM.HCl dihydrate was isolated by filtering.

The α-APM moiety in the crystals was 35.4 g. This weight corresponds to a 80.2% yield on the basis of the For-α-APM.

EXAMPLE 6

A mixture of 15 ml methanol, 65 ml 7N hydrochloric acid and 48.3 g For-α-APM was stirred at 20° C. for 4 days and then at 5° C. for 3 hours.

The precipitated α-APM.HCl dihydrate crystals were isolated by filtering.

The isolated crystals were dissolved in 600 ml water. The resulting solution was, after being adjusted in pH to 4.7 with sodium carbonate, allowed to stand overnight in a refrigerator.

The precipitated crystals were collected by filtering, washed with 100 ml cold water, and dried.

The yield was 32.6 g as α-APM.½H$_2$O (71.6% yield on the basis of the For-α-APM). $[\alpha]_D^{20} = +15.6°$ (c=4, 15N formic acid). The purity of the crystals was, when measured with the same amino acid analyser that was used in EXAMPLE 1, found to be over 98%.

EXAMPLE 7

A mixed solvent of 15 ml methanol, 25 ml water and 14 ml concentrated hydrochloric acid was heated to 70° C. 48.3 g For-α-APM was added to the heated solvent and the resulting mixture was kept at this temperature for 15 minutes. Thereafter, the mixture was rapidly cooled to 20° C., mixed with 14 ml concentrated hydrochloric acid, and stirred at 20° C. for 2 days and further at 5° C. for 3 hours.

The formed crystals were isolated from the remainder by filtering.

The α-APM moiety in the crystals was 34.3 g and corresponds to a 77.7% yield on the basis of the For-α-APM.

EXAMPLE 8

EXAMPLE 4 was repeated with the use of 10 ml methanol instead of 15 ml methanol.

The isolation yield of the α-APM.HCl dihydrate was 82.3% on the basis of the For-α-APM.

EXAMPLE 9

EXAMPLE 4 was repeated again but with the use of 20 ml methanol instead of 15 ml methanol.

The isolation yield of the α-APM.HCl.2H$_2$O was 73.6% on the basis of the For-α-APM.

EXAMPLE 10

A mixture of 18 ml methanol, 30 ml water and 17 ml concentrated hydrochloric acid was heated to 70° C. and added with 48.3 g For-α-APM. The resulting mixture was kept at this temperature for 10 minutes, rapidly cooled to 20° C., and, after added with 24 ml concentrated hydrochloric acid, stirred at 20° C. for 2 days and further at 5° C. for 3 hours.

The precipitated α-APM.HCl.2H$_2$O crystals were collected by filtering.

The α-APM moiety in the collected crystals was 33.1 g and corresponds to a 75.0% yield on the basis of the For-α-APM.

EXAMPLE 11-17

Some examples were carried out under the conditions given in Table 1, the other conditions being the same as in EXAMPLE 5. The results are also listed in the table.

TABLE 1

| EXAMPLE | Methanol (ml) | Water (ml) | conc. Hydrochloric Acid (ml) | Reaction Temp. (°C.) | Reaction Time (day) | Isolation Yield of $\alpha$-APM.HCl.2H$_2$O (based on For-$\alpha$-APM) (%) |
|---|---|---|---|---|---|---|
| 11 | 10 | 25 | 42 | 25 | 4 | 81.5 |
| 12 | 20 | 36 | 50 | 20 | 4 | 78.2 |
| 13 | 15 | 25 | 25 | 25 | 2 | 75.6 |
| 14 | 20 | 25 | 42 | 20 | 3 | 75.3 |
| 15 | 15 | 25 | 42 | 20 | 1 | 70.1 |
| 16 | 15 | 25 | 42 | 35 | 3 | 75.8 |
| 17 | 15 | 25 | 42 | 5 | 4 | 79.9 |

What is claimed is:

1. A process for selectively producing α-L-aspartyl-L-phenylalanine methyl ester or its hydrochloride, which comprises:

contacting N-formyl-α-L-aspartyl-L-phenylalanine methyl ester with a mixture of 7 to 12N aqueous hydrochloric acid and 5 to 60% by volume of methanol, based on the volume of the aqueous hydrochloric acid, at a temperature of between 0° and 40° C. for a time of from 1 to 5 days, whereby the amino-protecting formyl group is removed and α-L-aspartyl-L-phenylalanine methyl ester hydrochloride crystalizes; and isolating said hydrochloride from said mixture.

2. The process of claim 1, wherein said methanol concentration is from 10 to 30% by volume.

3. The process of claim 1, which comprises the additional step of converting said hydrochloride to α-L-aspartyl-L-phenylanine methyl ester.

4. A process for selectively producing α-L-aspartyl-L-phenylalanine methyl ester or its hydrochloride, which comprises:

maintaining a mixture of N-formyl-L-aspartyl-L-phenylalanine methyl ester, 7 to 12N aqueous hydrochloric acid, and 5 to 60% by volume of methanol, based on the volume of the aqueous hydrochloric acid, at a temperature between 50° and 100° C. for a period of time not longer than 30 minutes, cooling said mixture to a temperature between 0° and 40° C., maintaining said mixture at a temperature between 0° and 40° C. for from 1 to 3 days, whereby the amino-protecting formyl group is removed and α-L-aspartyl-L-phenylalanine methyl ester crystalizes, and isolating said hydrochloride from said mixture.

5. A process for selectively producing α-L-aspartyl-L-phenylalanine methyl ester or its hydrochloride, which comprises:

maintaining a mixture of N-formyl-α-L-aspartyl-L-phenylalanine methyl ester, 2 to 6N aqueous hydrochloric acid, and 10 to 70% by volume of methanol, based on the volume of the aqueous hydrochloric acid, at a temperature between 50° and 100° C. for a period of time not longer than 30 minutes, adding hydrochloric acid to said mixture to adjust the hydrochloric acid concentration in said mixture to a higher value between 7 to 12N, maintaining the resulting mixture at a temperature of between 0° and 40° C. for from 1 to 3 days, whereby the amino-protecting formyl group is removed while α-L-aspartyl-L-phenylalanine methyl ester crystalizes, and isolating said hydrochloride from said mixture.

6. The process of claim 5, wherein the concentration of methanol is from 30 to 55% by volume based on the volume of hydrochloric acid.

* * * * *